US012246006B2

(12) United States Patent
Terraz Mendoza et al.

(10) Patent No.: US 12,246,006 B2
(45) Date of Patent: Mar. 11, 2025

(54) SINGLE-DOSE PACKAGED CLOTRIMAZOLE LIQUID COMPOSITION

(71) Applicant: LABORATORIOS SALVAT, S.A., Esplugues De Llobregat (ES)

(72) Inventors: Maria Mar Terraz Mendoza, Esplugues de Llobregat (ES); Javier Sanagustín Aquilué, Esplugues de Llobregat (ES); Adolfo Téllez Molina, Esplugues de Llobregat (ES); María Isabel Delgado Gañán, Esplugues de Llobregat (ES)

(73) Assignee: LABORATORIOS SALVAT, S.A., Esplugues de Llobregat (ES)

( * ) Notice: Subject to any disclaimer, the term of this patent is extended or adjusted under 35 U.S.C. 154(b) by 828 days.

(21) Appl. No.: 17/310,260

(22) PCT Filed: Feb. 18, 2020

(86) PCT No.: PCT/EP2020/054250
§ 371 (c)(1),
(2) Date: Jul. 27, 2021

(87) PCT Pub. No.: WO2020/169611
PCT Pub. Date: Aug. 27, 2020

(65) Prior Publication Data
US 2022/0133695 A1 May 5, 2022

(30) Foreign Application Priority Data
Feb. 19, 2019 (EP) .................................... 19382120

(51) Int. Cl.
*A61K 31/4174* (2006.01)
*A61J 1/14* (2023.01)
*A61K 9/08* (2006.01)
*A61K 47/10* (2017.01)

(52) U.S. Cl.
CPC ......... *A61K 31/4174* (2013.01); *A61J 1/1468* (2015.05); *A61K 9/08* (2013.01); *A61K 47/10* (2013.01)

(58) Field of Classification Search
CPC ................................................ A61K 31/4174
See application file for complete search history.

(56) References Cited

U.S. PATENT DOCUMENTS

| 2009/0011045 A1 | 1/2009 | Mertin et al. |
| 2013/0338206 A1 | 12/2013 | Roberts et al. |
| 2015/0297588 A1 | 10/2015 | Branch et al. |

FOREIGN PATENT DOCUMENTS

| JP | S5598112 A | 7/1980 |
| JP | H05306223 A | 11/1993 |
| JP | 2007534384 A | 11/2007 |
| JP | 2010515509 A | 5/2010 |
| WO | WO 2005/102058 A2 | 11/2005 |
| WO | WO 2008/059261 A1 | 5/2008 |
| WO | WO 2008/084231 A1 | 7/2008 |
| WO | WO 2012/083138 A2 | 6/2012 |

OTHER PUBLICATIONS

Zadbuke et al., Recent trends in future of pharmaceutical packaging technology, J Pharm Bioallied Sci. 5(2): 98-110, 27 pages, (2013).*
International Search Report and Written Opinion mailed Apr. 17, 2020 for Application No. PCT/EP2020/054250, 15 pages.
Anonymous: "Canesten Solution—Summary of Product Characteristics", Bayer plc, Aug. 7, 2018; retrieved from the internet Jul. 23, 2019 URL: https://www.medicines.org.uk/emc/product/2209/smpc/print; XP055608030, 6 pages.
Mahalingam, et al: "Semisolid Dosages: Ointments, creams and gels", Pharmaceutical Manufacturing Handbook: Production and Processes; Jan. 1, 2010; pp. 267-312; XP055238546.
United States Pharmacopeia USP 41 "Clotrimazole Topical Solution" printed Feb. 15, 2019; pp. 1044-1045.
United States Pharmacopeia USP 41 <71> "Sterility Test" printed Feb. 15, 2019; pp. 5984-5991.
United States Pharmacopeia USP 41 <921> "Water Determination" printed Feb. 15, 2019; pp. 6687-6692.

* cited by examiner

*Primary Examiner* — Brian E McDowell
(74) *Attorney, Agent, or Firm* — Squire Patton Boggs (US) LLP

(57) ABSTRACT

It relates to a single-dose packaging unit which is a blow-fill-seal (BFS) container which comprises a sterile pharmaceutical or veterinary liquid composition which is a solution, wherein a) the composition comprises a therapeutically effective amount of clotrimazole or a pharmaceutically or veterinary acceptable salt thereof, together with one or more pharmaceutically or veterinary acceptable excipients or carriers, and b) the container has a volume from 0.05 to 8 mL, with the condition that the water content of the composition is equal to or lower than 4% by weight with respect to the total composition weight. It also relates to a secondary packaging comprising one or more single-dose packaging units.

17 Claims, No Drawings

SINGLE-DOSE PACKAGED CLOTRIMAZOLE LIQUID COMPOSITION

CROSS-REFERENCE

This application is a 35 USC 371 national phase filing of PCT/EP2020/054250 filed on Feb. 18, 2020, which claims the benefit of and priority to European Patent Application EP19382120.4 filed on Feb 2, 2019, both applications are incorporated herein by reference in their entirety.

TECHNICAL FIELD

The present invention belongs to the field of medicine and pharmaceutical packaging industry. In particular, it relates to a single-dose packaged liquid pharmaceutical or veterinary composition which comprises clotrimazole or a salt thereof, more particularly it relates to a clotrimazole composition placed in single-dose blow-fill-seal (BFS) containers.

BACKGROUND ART

Clotrimazole is the International Nonproprietary Name (INN) of the chemical compound 1-[(2-chlorophenyl)diphenylmethyl]imidazole. The CAS Registry number of clotrimazole is 23593-75-1 and its chemical structure is shown below:

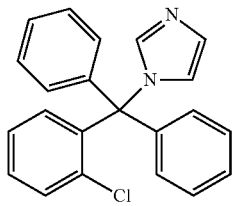 [SMILES: Clc1ccccc1C(c1ccccc1)(c1ccccc1)n1ccnc1]

Clotrimazole shows a broad-spectrum antifungal activity. Its mechanism of action is based on the inhibition of the biosynthesis of sterols, particularly ergosterol, required for cell membrane production, thus altering the permeability of the fungal cell wall, and eventually causing cell lysis.

Clotrimazole is a well-established drug used in dermatology and gynaecology. It is available under a variety of formulations including creams (e.g. oil and water emulsions), tablets, capsules, pessaries, sprays and solutions.

Among the approved liquid formulations, mention can be made for example, of the 1.0% w/v solution of clotrimazole in Macrogol 400, which is approved for the treatment of all fungal skin infections due to dermatophytes, yeasts, moulds and other fungi, and is particularly suitable for use on hairy skin and in fungal infections of the outer ear (otitis externa) and middle ear (otomycoses). This clotrimazole solution is contained in a 20 mL multi-dose container made of high density polyethylene (HDPE) bottles having a dropper insert and screw-on cap. However, this solution is not sterile.

It is known that otitis externa may result in tympanic membrane perforations. Therefore, for safety reasons, the US Food and Drug Administration (FDA) requires that the otic medications to be applied in not intact tympanic membrane must be sterilized.

In case of multi-dose containers, such as the one mentioned above, one option to prevent contamination of the composition after opening the container is to include preservatives in the formulation. However, it is well-known that preservatives may be irritant and/or not well tolerated by patients, especially when the formulations are applied in sensitive skin areas or mucosae.

Unlike multi-dose containers, single-dose containers hold a drug composition in an amount which is intended for single-dose administration. Once the single-dose container is opened it cannot be resealed. Besides, the fact that the drug is promptly used after opening the container assures sterility of the formulation until use. Thus, single-dose containers containing sterile clotrimazole otic solutions are an interesting option to be developed taking into account the FDA requirements. However, there is currently no approved product based on a clotrimazole solution which is contained in a disposable packaging for single-use.

Several techniques of sterilization are known in the art. For example, sterility may be achieved by exposing the formulation to be sterilized to elevated temperature (heat sterilization), ionizing radiation (radiation sterilization), chemical liquids or gases (liquid or gaseous sterilization), or by filtering the composition (filtration sterilization). Traditional aseptic processing allows a final sterile drug product to be achieved by individually sterilizing the containers, material and equipment in-process, resulting in a unified sterilized product. In traditional aseptic processing, the containers are either supplied cleaned and sterilized to the filling line, or they are cleaned and sterilized within the aseptic filling line. Plastic containers are usually washed, dried, sterilized and cooled before filling. Methods of sterilization used in aseptic processing include filtering the solution by dissolving it in a solvent, such as Water For Injection (WFI), where the solution is passed through a sterilizing filter or membrane. Filter sterilization is used where the component is soluble and likely to be adversely affected by heat. Dry heat sterilization is another effective method for sterilizing components that are heat stable and insoluble. Irradiation can also be used to sterilize some components. Traditional aseptic processing, involving filling open glass bottles or vials, requires that the manufacturer maintain aseptic conditions in critical processing areas at all times. Unfortunately, the majority of liquid drug product contamination over the past several decades has come about from products produced in traditional aseptic processing facilities. Endotoxins are a potential pyrogenic contaminant, essentially related to dead bacterial cellular matter that can lead to serious reactions in patients, being a safety concern to be seriously considered in the manufacture of sterile drug products.

On the other hand, the Blow-Fill-Seal (BFS) technology is now widely considered to be the preferred form of aseptic processing of drug compositions by various medicine regulatory agencies including the FDA. The BFS technique, which is a continuous process without human intervention in a sterile enclosed area inside a machine, includes the steps of "forming" the container which has to contain the sterile drug composition (e.g., by blowing into a mould), "filling" it with the drug composition, and "sealing" it. Thus, this technology can be used to aseptically manufacture sterile pharmaceutical liquid formulations.

US20090011045 discloses pharmaceutical compositions, in particular suspensions, containing an anti-infective agent in a liquid base aliquoted in a primary packaging means, in particular tubes, for once-only administration. However, this document does not teach single-dose compositions packaged in blow-fill-seal (BFS) containers. The compositions disclosed in this document may further contain an antimycotic agent such as clotrimazole, which is typically employed in the formulation in a proportion of 0.01-10% by weight. Water may be used as auxiliary substance. In particular, US20090011045 discloses that water, glycerol, propylene glycol or polyethylene glycols can be used as the aqueous base. Alternatively, natural animal or vegetable, synthetic and semisynthetic oils or fats can be used as the oily base. Furthermore, the suspensions generally contain preservatives and/or antioxidants, and are not sterilized. Besides, this document does not disclose any stability data of the compositions contained in the single-dose containers.

US20150297588 discloses sterile otic formulations comprising an antibacterial agent and an antifungal, such as clotrimazole. The formulations disclosed in this document include a carrier, for example a mineral oil, which contains a thickener, such as wax. It is also disclosed that clotrimazole is heat-sterilized in the mixture of wax and mineral oil to 121° C. for 1.5 h, and that once the components of the formulation have been sterilized, they are mixed and homogenized and added to syringes under sterile conditions. According to the inventors of US20150297588, only one administration of the thick suspension is required to eradicate a spectrum of fungal and bacterial infections and the coincident inflammation. However, this document does not teach single-dose packaged compositions, and even less single-dose compositions packaged in blow-fill-seal (BFS) containers.

Besides, the semisolid formulations described in US20150297588 have several drawbacks. First of all, as acknowledged by the inventors of that patent application, patient's hearing is affected due to the administration of the suspension, and it takes them within 5 to 7 days after treatment to recover normal hearing. In fact, since the formulation remains in the ear canal for several days it is likely to cause undesired side-effects such as pain, itch, and dizziness. Additionally, as acknowledged by the inventors of US20150297588, the suspension cannot be administered by the patient itself but requires the intervention of a doctor.

Finally, the inventors of US20150297588 conclude that clotrimazole did not show any significant degradation. However, the heat sterilization treatment not only may affect the stability of the active ingredients but also the stability of the excipients. In this regard, it is known for example that thickeners such as paraffins, which are included in the compositions referred in US20150297588, have to be stored at a temperature not exceeding 40° C. in well-closed containers, as well as many other excipients that may be unstable during sterilization by dry heat or radiation processes. Accordingly, these types of excipients would not be suitable for carrying out heat or radiation sterilization treatments.

In US20150297588 it is disclosed that stratification or separation of phases at room temperature was observed in the formulations. This could be a hint that the sterilization process was not adequate for the excipients, or that the system was not stable per se at room temperature. In any case, it is clear that a product that is only stabilized below 20° C. has a clear disadvantage when marketing the product. When the phases are separated, the active principle loses its homogeneity and when applied to the ear canal it will be heterogeneously distributed being potentially accumulated in some areas or inexistent in others. Besides, the inventors of US20150297588 acknowledge that the analysis of top and bottom layer indicates that the content of active ingredients is not homogenous and in some instances the active ingredients appear to have been settling at the bottom of the container. The referred lack of stability of these suspensions by the phase separation may be a problem during administration of the suspension into the ear cavity, since part of the active agent may be retained in the syringe in solid form thereby resulting in a loss of efficacy.

Therefore, there is still a need of developing sterile single-dose packaged clotrimazole liquid formulations, which overcome the problems of the prior art.

SUMMARY OF INVENTION

As mentioned above, the development of sterile single-dose packaged clotrimazole liquid compositions, in particular prepared by blow-fill-seal (BFS) technology, is of especial interest taking into account the regulatory requirements of sterility of otic products to treat infections with potential affectation of tympanic membrane.

An important characteristic of the Blow-Fill-Seal process is the sterile and pyrogen-free moulding of the bottles or ampoules directly from the extruded plastic or resin in water cooled blow moulds with an immediate sterile filling of product, followed by a hermetic sealing of the container in one step and under aseptic conditions in the same machine. This assures a high reliability of the process as well as product security. The technology is known for a very low particulate matter production and neutrality to the filling product. A critical aspect of BFS technology is its pyrogen-free moulding of containers and ampoules. Extensive experiments confirming the efficacy of the BFS extrusion process have been performed using high levels of spores and endotoxin-contaminated polymer granules. The typical BFS extruders have demonstrated spore contamination rates of 0.000001 percent, and 0.00001 percent for endotoxins, currently being the best technological approach to manufacture sterile solutions.

Typically, the standard BFS process includes the steps of extruding a polymer or polymer mixture which will form the container or primary packaging, moulding, filling, sealing, and demoulding it. In the BFS process the product-contact path is sterilized with pressurized steam to reduce possible contamination, and then dried with sterile-filtered air by automatic programs. Other sterilization methods for sterilizing the BFS system have been described such as sterilization with nitrogen dioxide gas in the presence of air and water vapor (80% moisture). However, this method is rarely used industrially due to the by-products derived from it.

When trying to prepare single-dose packaged BFS compositions under the above-mentioned standard process conditions, the present inventors surprisingly observed a significant increase of the clotrimazole-related impurities imidazole and (2-chlorophenyl)-diphenylmethanol. This degradation of clotrimazole was completely unexpected to the present inventors because no stability problems had been encountered for the multi-dose containers made of the same polymeric materials and containing a clotrimazole liquid composition with exactly the same excipients (see comparative example 2 below).

Without being bound to theory, it seems that when the same composition of the multi-dose container is placed in a single-dose container, certain specific conditions appear that unexpectedly change the stability of the product.

After carrying out a development program aimed at solving the above stability issues in these single-dose BFS containers, the present inventors found that when the single-dose packaged compositions were placed under inert-like conditions, in particular by controlling the water content of the composition inside the single-dose packaging under a certain level, the composition was stable during storage. This solution was surprising to the present inventors. In fact, a skilled person would not have seen the presence of water as a restraint because the clotrimazole compositions described in US20090011045 or US20150297588 may include high amounts of water, and because there are clotrimazole products based on aqueous emulsions on the market, which are stable.

Thus, the present invention provides a safe single-dose packaged clotrimazole liquid composition which is sterile, homogeneous, and stable without the presence of preservatives which may cause undesired side-effects. The single-dose packaged composition of the invention allows administering a more exact dose. This has the advantage that it may reduce medication errors and improve patient compliance. In addition, it allows hygienic administration and it does not need to be administered by health professionals.

Therefore, an aspect of the present invention relates to a single-dose packaging unit which is a blow-fill-seal (BFS) container which comprises a pharmaceutical or veterinary liquid composition, wherein the composition comprises a therapeutically effective amount of clotrimazole or a pharmaceutically or veterinary acceptable salt thereof, together with one or more pharmaceutically or veterinary acceptable excipients or carriers, with the condition that the water content of the composition is equal to or lower than 4% by weight with respect to the total composition weight. In particular, the liquid composition is sterile and/or is a solution, and/or the container has a volume from 0.05 to 8 mL.

One or more of the BFS single-dose packaging units of the invention may be packaged in a secondary packaging. The inventors found that when the single-dose BFS container containing the sterile clotrimazole liquid composition was placed in a secondary packaging and the oxygen content inside this secondary packaging was controlled, the stability of the composition was even improved. Thus, the present invention also relates to a secondary packaging comprising one or more single-dose packaging units as previously defined, and more particularly, to a secondary packaging wherein the oxygen content inside the secondary packaging is equal to or lower than 10% by volume with respect to the total gas volume.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply throughout the description and claims.

The term "about" or "around" as used herein refers to a range of values ±10% of a specified value. For example, the expression "about 10" or "around 10" includes ±10% of 10, i.e. from 9 to 11.

Unless otherwise stated, all percentages mentioned herein regarding water content are expressed in weight with respect to the total weight of the composition. The percentages mentioned herein regarding components of the compositions are expressed in weight with respect to either the total volume or the total weight of the composition, provided that the sum of the amounts of the components is equal to 100% content. Regarding oxygen content, the volume percentage of this gas in atmospheric air by volume is 20.946% or 209.46 ppmv. All percentages mentioned herein regarding oxygen content are equally referred to the volume percentage of oxygen regarding the total volume of air or gas content included in the secondary packaging.

As mentioned above, the invention relates to a single-dose packaging unit which is a blow-fill-seal (BFS) container and which comprises a liquid clotrimazole composition.

For the purposes of the invention, the expressions "single-dose packaged composition" and "single-dose packaging unit which comprises a composition" refer to the fact that the composition is placed in a single-dose packaging unit or container and is intended for single-use. Single-dose containers cannot be resealed after having been opened. Therefore, they are disposable and cannot be reused. The term single-dose packaging can also be referred to as monodose packaging. The "single-dose packaging" may be also referred to as the primary packaging.

In one embodiment, optionally in combination with one or more features of the various embodiments described above or below, the single-dose packaging unit as defined above is disposable.

The term "primary packaging" as used herein refers to the packaging which is in direct contact with the clotrimazole liquid composition. By contrast, the term "secondary packaging" refers to the packaging that is not in direct contact with the clotrimazole formulation but contains the primary packaging.

The term "blow-fill-seal (BFS) container" refers to the container that has been prepared by BFS technology. The term "BFS" refers to a process without the need of any external intervention which begins with the extrusion of polymer granules of molten polymer or resin. Then, a container is formed from the polymer granules by blow moulding them, e.g. by using sterile compressed air, by vacuum or both. After that, the formed container, which is still in a molten state and is open from the top, is filled with the clotrimazole composition, e.g. by filling nozzles which enter from the top of container. Finally, the top of the container is sealed and cooled, giving rise to a hermetically sealed container. The BFS container of the invention is made of a polymer or polymer mixture.

The BFS container of the invention is generally a small container, typically having a volume from 0.05 to 8 mL. The BFS containers may have different shapes. Non-limiting examples of BFS containers include vials and ampoules.

In one embodiment, optionally in combination with one or more features of the various embodiments described above or below, the BFS container has a volume from 0.05 to 8 mL, more particularly from 0.05 to 5 mL, even more particularly from 0.10 to 3 mL, and even more particularly from 0.15 to 0.9 mL.

The single-dose packaging unit of the invention comprises a liquid composition which comprises a therapeutically effective amount of clotrimazole or a pharmaceutically or veterinary acceptable salt thereof.

For the purposes of the invention, the term "liquid composition" refers to any clotrimazole composition which is not in solid form and whose viscosity, measured using a RVDV-III Ultra Brookfield rheometer at 25° C. at a spindle speed of 10 rpm after 5 minutes of rotation, is equal to or less than 2000 mPa·s, more particularly is from 10 mPa·s to 1000 mPa·s. The liquid composition of the invention may be a solution.

In one embodiment, optionally in combination with one or more features of the various embodiments described above or below, the liquid composition is a solution, where all components are fully solubilized forming a homogeneous solution. This dosage form advantageously provides improved bioavailability in comparison to other heterogeneous liquid compositions. Generally, the bioavailability of the products administered in the form of a suspension is lower than that of the solubilized products. In fact, it is widely recognized that the solubilization of insoluble active ingredients drugs is one of the challenges of the formulator to improve its bioavailability, especially in topical systems, where there is no digestive process that promotes the release and absorption of the active ingredient.

The expression "therapeutically effective amount" as used herein, refers to the amount of clotrimazole that, when administered, is sufficient to prevent development of, or alleviate to some extent, one or more of the symptoms of the disease which is addressed. The specific dose of clotrimazole to obtain a therapeutic benefit may vary depending on the particular circumstances of the individual patient including, among others, the size, weight, age and sex of the patient, the nature and stage of the disease, the aggressiveness of the disease, and the route of administration.

In one embodiment, optionally in combination with one or more features of the various embodiments described above or below, the therapeutically effective amount of clotrimazole is from 0.1 to 5% by weight, more particularly from 0.5 to 2.5% by weight, even more particularly is about 1% by weight, with respect to the total composition volume.

In one embodiment, optionally in combination with one or more features of the various embodiments described above or below, clotrimazole is the single active ingredient of the composition of the invention.

There is no limitation on the type of clotrimazole salt that can be used, provided that the salt is pharmaceutically or veterinary acceptable when used for therapeutic purposes. The term "pharmaceutically or veterinary acceptable salt", embraces salts commonly used. The preparation of clotrimazole pharmaceutically acceptable salts can be carried out by methods known in the art. Clotrimazole and its salts may differ in some physical properties, but they are equivalent for the purposes of the present invention. Non-limiting examples of pharmaceutically or veterinary acceptable salts of clotrimazole include salts of organic or inorganic acids such as hydrochloric acid, hydrobromic acid, hydroiodic acid, sulfuric acid, nitric acid, phosphoric acid, acetic acid, succinic acid, oxalic acid, malic acid, adipic acid, dihydroxybenzoic acid (e.g. 2,5-dihydroxybenzoic acid), trihydroxybenzoic acid (e.g. 2,4,6-trihydroxybenzoic acid), coumaric acid (e.g. p-coumaric acid), caffeic acid, maleic acid, and suberic acid, and the like.

Crystalline forms of clotrimazole are also encompassed in the formulations of the present invention. Crystalline forms of clotrimazole may exist either as free solvation forms or as solvates (e.g. hydrates) and it is intended that both forms are within the scope of the present invention. Methods of solvation are generally known within the art. In general, the solvated forms with pharmaceutically or veterinary acceptable solvents such as water, ethanol and the like are equivalent to the unsolvated form for the purposes of the invention. Co-crystals of clotrimazole with pharmaceutically or veterinary acceptable coformers are also encompassed in the formulations of the present invention and are equivalent to clotrimazol or its salts for the purposes of the invention. Non-limiting examples of co-crystals include co-crystals with carboxylic acid conformers such as for example clotrimazole-adipic acid cocrystal (1:0.5), and clotrimazole-suberic acid cocrystal (1:0.5).

The liquid composition of the invention may be sterilized. Sterilization is the process of removal or deactivation of all forms of life and other biological agents present in a drug composition. The terms "sterile or sterilized" composition are used herein interchangeably and refer to a composition that does not present microbial and/or fungal contamination, in particular order to comply with USP 41 <71> Sterility Test (no evidence of microbial growth). For the purposes of the invention sterility means the absence of viable microorganisms, as defined by a sterility assurance level (SAL) equal to or less than $10^{-6}$. The sterility assurance level SAL for a given sterilization process is expressed as the probability of microorganisms (bacteria, yeasts, and molds) surviving in a product item after exposure to the process. An SAL of $10^{-6}$, for example, denotes a probability of not more than 1 nonsterile item in $1 \times 10^6$ sterilized items of the final product.

Although different sterilization methods may be used, the filtration sterilization method has the advantage that the composition containing clotrimazole and excipients and/or carriers is not heated or irradiated, thus limiting any possible degradation related to high temperature or irradiation. Noteworthy heat or radiation methods destroy microorganisms, but destructed debris remain inside the final product. The filtration sterilization removes microorganisms and other foreign biological subproducts from solutions. In such process, the composition to be sterilized is filtered through a membrane filter, e.g. made of homogenous polymers of mixed cellulosic esters, polyvinylidene fluoride, or polytetrafluoroethylene, and the like, which have pore sizes ranging from 0.1 to 0.22 µm. Sterilization by filtration is considered the most reliable method regarding removal of endotoxins, which are a potential pyrogenic contaminant, essentially coming from dead bacterial cellular matter. Furthermore, extensive experiments have confirmed the efficacy of the sterilization by sterilization process even in the elimination of spores and endotoxins contamination, being a clear advantage over other old conventional sterilization processes.

In one embodiment, optionally in combination with one or more features of the various embodiments described above or below, the liquid composition is a sterile composition, more particularly a composition which has been sterilized by filtration. More particularly, the sterile composition of the invention is obtainable by a process comprising a sterilization step of filtering the composition, more particularly using one or more sterilization filters, and even more particularly, polyvinylidene difluoride (PVDF) membrane filters of pore size about 0.22 µm.

In one embodiment, optionally in combination with one or more features of the various embodiments described above or below, the invention relates to a single-dose packaging unit which is a blow-fill-seal (BFS) container which comprises a sterile pharmaceutical or veterinary liquid composition which is a solution, wherein:
a) the composition comprises a therapeutically effective amount of clotrimazole or a pharmaceutically or veterinary acceptable salt thereof, together with one or more pharmaceutically or veterinary acceptable excipients or carriers, and
b) the container has a volume from 0.05 to 8 mL,
with the condition that the water content of the composition is equal to or lower than 4% by weight with respect to the total composition weight.

The single-dose packaged composition of the invention comprises clotrimazole or a salt thereof together with one or more pharmaceutically or veterinary acceptable excipients or carriers.

The expression "pharmaceutically or veterinary acceptable excipients or carriers" refers to pharmaceutically or veterinary acceptable materials, compositions or vehicles. Each component must be pharmaceutically or veterinary acceptable in the sense of being compatible with the other ingredients of the pharmaceutical or veterinary composition.

It must also be suitable for use in contact with the tissue or organ of humans and animals without excessive toxicity, irritation, allergic response, immunogenicity or other problems or complications commensurate with a reasonable benefit/risk ratio.

The appropriate excipients and/or carriers, and their amounts, can readily be determined by those skilled in the art according to the type of formulation being prepared.

The composition of the invention is suitable for otic administration. Thus, in one embodiment, optionally in combination with one or more features of the various embodiments described above or below, the liquid composition is an otic formulation to be administered to the ear canal, in particular to the outer and/or middle ear. The single-dose packaged liquid composition of the invention has the advantage that it does not affect hearing abilities.

The single-dose packaged compositions of the invention are useful in the treatment of all fungal skin infections due to dermatophytes, yeasts, moulds and other fungi, and are particularly suitable for use in fungal infections of the outer ear (otitis externa) and middle ear (otomycoses).

In one embodiment, optionally in combination with one or more features of the various embodiments described above or below, the liquid composition comprises a solubilizing agent.

For the purposes of the invention, the term "solubilizing agent" refers to an agent or combination of agents that are able to solubilize clotrimazole or its salts, thereby forming a homogeneous solution. Examples of solubilizing agents include, without limitation, oils, ($C_1$-$C_{18}$) alkyl esters of ($C_4$-$C_{28}$) fatty acids, glycerides, and polyhydric alcohols.

The term "oil" as used herein relates to a wide class of substances typically unctuous, viscous and liquid at room temperature (20-25° C.), which can be from animal, mineral, vegetable or synthetic origin. Examples of oils include, without limitation, liquid paraffin, light liquid paraffin, argan oil, corn oil, palm oil, coconut oil, cottonseed oil, peanut oil, rapeseed oil, sunflower oil, sesame oil, soybean oil, safflower oil, almond oil, castor oil, and olive oil.

The term "($C_4$-$C_{28}$) fatty acid" as used herein refers to a carboxylic acid with a long aliphatic chain, which is either linear or branched, saturated or unsaturated, and contains from 4 to 28 carbon atoms. Examples of fatty acids include, without limitation, stearic acid, cerotic acid, isostearic acid, palmitic acid, oleic acid, linoleic acid, myristic acid, behenic acid, arachidic acid, montanic acid, capric acid, caprylic acid and lauric acid.

The term "alkyl" as used herein refers to a saturated, branched or linear alkyl chain which contains the number of carbon atoms specified in the present description.

Examples of ($C_1$-$C_{18}$) alkyl esters of ($C_4$-$C_{28}$) fatty acids include, without limitation, ethyl oleate, decyl oleate, isopropyl myristate, isopropyl palmitate, isopropyl isostearate, isostearyl isostearate, and myristyl lactate.

The term "glycerides" as used herein refers to esters formed from glycerol and ($C_4$-$C_{28}$) fatty acids. Depending on the number of the hydroxyl functional groups of the glycerol that are esterified, glycerides are classified as monoglycerides, including 1-monoacylglycerols and 2-monoacylglycerols; diglycerides, including 1,2-diacylglycerols and 1,3-diacylglycerols; and triglycerides, including medium chain triglycerides. The term "medium chain triglycerides" as used herein refers to triesters of glycerol and ($C_8$-$C_{12}$) fatty acids, wherein each of the three fatty acid residues may be the same or different.

Examples of medium chain fatty acids include, without limitation, caprylic triglyceride, caprylic/capric triglyceride, caproic triglyceride, capric acid triglyceride, lauric triglyceride, lauric/caprylic/capric triglycerides and the like.

The term "polyhydric alcohol" as used herein refers to an alcohol containing from 2 to 6 hydroxyl groups. Examples of polyhydric alcohols include, without limitation, ethylene glycol, diethylene glycol, triethylene glycol, polyethylene glycols, propylene glycol, dipropylene glycol, polypropylene glycols, butylene glycols, glycerol, diglycerol, and polyglycerols.

The term "polyethylene glycol (PEG)" as used herein is also referred to as macrogol, and has the general formula HO—(CH$_2$—CH$_2$—O)$_n$—H, wherein n is from 4 to 25. PEG may also be designated in combination with a numeric suffix which indicates the average molecular weight of the PEG. The PEG as used in the present invention has an average molecular weight from 150 to 1050 Daltons, more particularly from 150 to 550 Daltons. Examples of PEG include, without limitation, PEG 200, PEG 300, PEG 400 and PEG 600, and mixtures thereof.

In one embodiment, optionally in combination with one or more features of the various embodiments described above or below, the solubilizing agent is selected from the group consisting of oils, ($C_1$-$C_{18}$) alkyl esters of ($C_4$-$C_{28}$) fatty acids, glycerides, polyhydric alcohols, and mixtures thereof. More particularly, the solubilizing agent is selected from the group consisting of liquid paraffin, light liquid paraffin, argan oil, corn oil, palm oil, coconut oil, cottonseed oil, peanut oil, rapeseed oil, sunflower oil, sesame oil, soybean oil, safflower oil, almond oil, castor oil, olive oil, ethyl oleate, decyl oleate, isopropyl myristate, isopropyl palmitate, isopropyl isostearate, isostearyl isostearate, myristyl lactate, caprylic triglyceride, caprylic/capric triglyceride, caproic triglyceride, capric acid triglyceride, lauric triglyceride, lauric/caprylic/capric triglyceride, ethylene glycol, diethylene glycol, triethylene glycol, polyethylene glycols, propylene glycol, dipropylene glycol, polypropylene glycols, butylene glycols, glycerol, diglycerol, polyglycerols, and mixtures thereof. Even more particularly, the solubilizing agent is selected from the group consisting of liquid paraffin, isopropyl myristate, capric/caprylic triglycerides, castor oil, or polyethylene glycol, and even more particularly is selected from the group consisting of polyethylene glycol, such as PEG 200, PEG 300, PEG 400, PEG 600, and mixtures thereof.

In another embodiment, optionally in combination with one or more features of the various embodiments described above or below, the liquid composition of the invention consists of clotrimazol or a salt thereof and a solubilizing agent, as defined above.

Alternatively, the liquid composition of the invention may comprise further excipients such as surfactants, emulsifiers, thickening agents, colorants, flavoring agents, etc.

As previously mentioned, the BFS container of the invention is made of polymers or blow mouldable resins. In one embodiment, optionally in combination with one or more features of the various embodiments described above or below, the blow-fill-seal (BFS) container is made of a polymer, more particularly a thermoplastic polymer o mixture of thermoplastic polymers.

In one embodiment, optionally in combination with one or more features of the various embodiments described above or below, the single-dose packaging unit is obtainable by a process comprising blow moulding a polymer or polymer mixture, in particular a thermoplastic polymer or a mixture of thermoplastic polymers, to form the container, filling it with the composition with a water content equal to or lower than 4% by weight, and sealing it, wherein all the steps of the process are performed in one single machine (BFS machine).

For the purposes of the invention, the term "thermoplastic polymer" refers to a polymer that turns to a liquid or becomes more liquid or less viscous when heated and can be moulded to a specific shape, e.g. by the application of heat and pressure. Examples of thermoplastic polymers include, without limitation, polyethylene (PE), polypropylene (PP), polybutylene, polyvinyl chloride (PVC), polystyrene (PS), polymethylmethacrylate (PMMA), combinations and copolymers of these substances. Different types of polyethylene may be used, including low density polyethylene (LDPE) (density: 0.910 to 0.940 g/cm$^3$), and high density polyethylene (HDPE) (density: 0.930-0.970 g/cm$^3$).

In one embodiment, optionally in combination with one or more features of the various embodiments described above or below, the thermoplastic polymer is selected from the group consisting of polyethylene (PE), polypropylene (PP), polybutylene, polyvinyl chloride (PVC), polystyrene (PS), polymethylmethacrylate (PMMA), combinations and copolymers of these substances, more particularly is selected from the group consisting of polyethylene (PE), LDPE, HDPE, polypropylene (PP), and copolymers and mixtures thereof; even more particularly is selected from the group consisting of polyethylene (PE), LDPE, HDPE, and mixtures thereof.

In one embodiment, optionally in combination with one or more features of the various embodiments described above or below, the single-dose packaging unit is hermetically sealed.

In one embodiment, optionally in combination with one or more features of the various embodiments described above or below, the single-dose packaging unit is obtainable by a process comprising a sterilization step of the path used for filling the container (i.e. product-contact path) with steam, in particular pressurized steam.

In one embodiment, optionally in combination with one or more features of the various embodiments described above or below, the single-dose packaging unit as defined above is obtainable by a process comprising the steps of:
 i) providing the clotrimazole pharmaceutical or veterinary liquid composition, particularly in the form of a solution, in a recipient,
 ii) sterilizing with steam the path of the BFS machine through which the composition has to be circulated,
 iii) blow moulding a polymer or polymer mixture, in particular a thermoplastic polymer or a mixture of thermoplastic polymers, to form a container, particularly having a volume from 0.05 to 8 mL,
 iv) selecting the composition of step i) such that its content of water originated from step ii) is equal to or lower than 4%, in particular is from 0.001 to 4%, by weight with respect to the total composition weight,
 v) filling the container formed in step iii) with the composition of step iv) through the sterilized path of step ii), and
 vi) sealing the container,
wherein the process steps ii) to vi) are carried out in one single machine (BFS machine).

In one embodiment, optionally in combination with one or more features of the various embodiments described above or below, the composition of step i) is sterilized by filtration; more particularly by using one or more sterilization filters, and even more particularly, by using one or more polyvinylidene difluoride (PVDF) membrane filters of pore size about 0.22 μm.

In one embodiment, optionally in combination with one or more features of the various embodiments described above or below, step iv) is performed by circulating the liquid composition of step i) through the sterilized path of step ii) and discarding composition until its water content is equal to or lower than 4%, in particular is from 0.001 to 4%, by weight with respect to the total composition weight. The amount of composition to be discarded depends from the volume of composition in a given batch. A skilled person may easily determine such volume by discarding a first volume, measuring the water content of the resulting composition in the container by Karl Fischer, and, if the water content is higher than 4%, discarding more composition until the desired water content is achieved.

As mentioned above, in order to achieve the desired storage stability, the water content of the composition inside the single-dose packaging has to be controlled such that it is equal to or lower than 4% by weight with respect to the total composition weight.

The expression "stable" composition refers to the fact that the composition does not show significant degradation products over time. More particularly, it means that the content of degradation impurities of clotrimazole, in particular imidazole and (2-chlorophenyl)-diphenylmethanol, is equal to or lower than 0.5% by weight with respect to the labeled amount of clotrimazole weight, and that the overall content of degradation products does not exceed 2.0% by weight with respect to the labeled amount of clotrimazole by weight, when the composition is placed under accelerated storage conditions (40° C., <25% relative humidity (RH)) for a period of at least 1 month, preferably 2 months. The labeled amount of clotrimazole is the weight amount of clotrimazol with respect to the total composition weight. The compositions of the invention are also stable when stored at room temperature (20-25° C.) for longer periods of time. Stability may be measured by using high performance liquid chromatography with ultraviolet detection (HPLC-UV), based on the analytical methodology described in the USP 41 (monograph 'Clotrimazole Topical Solution').

In particular, according to this monograph, the percentage of the labeled amount of clotrimazole in the portion of sample solution may be calculated by the following equation:

$$\text{Result} = (r_u/r_s) \times (C_s/C_u) \times 100$$

wherein:
$r_u$=peak response of clotrimazole from the sample solution
$r_s$=peak response of clotrimazole from the standard solution
$C_s$=concentration of clotrimazole in the standard solution (mg/mL)
$C_u$=nominal concentration of clotrimazole in the sample solution (mg/mL)

In the equation above, the standard and sample solutions are prepared at 0.2 mg/ml of clotrimazole in acetonitrile: water 50:50.

The percentage of the labeled amount of imidazole and (2-chlorophenyl)diphenylmethanol (clotrimazole related compound A) in the portion of sample solution, may be calculated by the following equation:

$$\text{Result} = (r_u/r_s) \times (C_s/C_u) \times 100$$

wherein:
$r_u$=peak response of clotrimazole related compound A or imidazole from the sample solution
$r_s$=peak response of clotrimazole related compound A or imidazole from the standard solution $C_s$=concentration of clotrimazole related compound A or imidazole in the standard solution (mg/mL)
$C_u$=nominal concentration of clotrimazole in the sample solution (mg/mL)

In the equation above, the standard solution corresponds to a solution containing 0.2 mg/mL of clotrimazole, and 0.001 mg/mL each of imidazole, and clotrimazole related compound A in acetonitrile:water 50:50.

The percentage of any unspecified impurity in the portion of sample solution, may be calculated by the following equation:

$$\text{Result}=(r_u/r_s)\times(C_s/C_u)\times100$$

wherein:
$r_u$=peak response of any unspecified impurity from the sample solution
$r_s$=peak response of clotrimazole from the standard solution
$C_s$=concentration of clotrimazole in the standard solution (mg/mL)
$C_u$=nominal concentration of clotrimazole in the Sample solution (mg/mL)

In the equation above, the standard solution corresponds to a solution containing 0. 2 mg/mL of clotrimazole, and 0.001 mg/mL each of imidazole, and clotrimazole related compound A in acetonitrile:water 50:50.

Total impurities are calculated as the sum of individual impurities.

In one embodiment, optionally in combination with one or more features of the various embodiments described above or below, the content of imidazole in the composition is equal to or lower than 0.5% by weight with respect to the labeled amount of clotrimazole by weight. More particularly, the content of imidazole in the composition is equal to or lower than 0.5% by weight with respect to the labeled amount of clotrimazole by weight after storage of the composition at 40° C., <25% RH over a 2-month period, or at room temperature over a 30-month period.

In one embodiment, optionally in combination with one or more features of the various embodiments described above or below, the content of (2-chlorophenyl)-diphenyl-methanol in the composition is equal to or lower than 0.5% by weight with respect to the labeled amount of clotrimazole by weight. More particularly, the content of (2-chlorophenyl)-diphenylmethanol in the composition is equal to or lower than 0.5% by weight with respect to the labeled amount of clotrimazole by weight after storage of the composition at 40° C., <25% RH over a 2-month period, or at room temperature over a 30-month period.

In one embodiment, optionally in combination with one or more features of the various embodiments described above or below, the water content of the composition is equal to or lower than 3.5%, equal to or lower than 3%, equal to or lower than 2.5%, equal to or lower than 2%, equal to or lower than 1.5%, equal to or lower than 1%, equal to or lower than 0.5%, equal to or lower than 0.2%, equal to or lower than 0.1%, equal to or lower than 0.05%, equal to or lower than 0.01%, equal to or lower than 0.005%, or equal to or lower than 0.001%, by weight with respect to the total composition weight. In another embodiment, optionally in combination with one or more features of the various embodiments described above or below, water is present in the composition and its content is equal to or lower than 3.5%, equal to or lower than 3%, equal to or lower than 2.5%, equal to or lower than 2%, equal to or lower than 1.5%, equal to or lower than 1%, equal to or lower than 0.5%, equal to or lower than 0.2%, equal to or lower than 0.1%, equal to or lower than 0.05%, equal to or lower than 0.01%, equal to or lower than 0.005%, or equal to or lower than 0.001%, by weight with respect to the total composition weight. In another embodiment, optionally in combination with one or more features of the various embodiments described above or below, the water content of the composition is from 0.001 to 4%, from 0.001 to 3.5%, from 0.001 to 3%, from 0.001 to 2.5%, from 0.001 to 2%, from 0.001 to 1.5%, from 0.001 to 1%, from 0.001 to 0.5%, from 0.001 to 0.2%, from 0.001 to 0.1%, from 0.001 to 0.005%, from 0.01 to 4%, from 0.01 to 3.5%, from 0.01 to 3%, from 0.01 to 2.5%, from 0.01 to 2%, from 0.01 to 1.5%, from 0.01 to 1%, from 0.01 to 0.5%, from 0.01 to 0.2%, from 0.01 to 0.1% or from 0.01 to 0.05%, by weight with respect to the total composition weight.

The water content of the composition (i.e. inside the single-dose packaging) may be measured by Karl Fischer, in particular by the method USP 41 <921> Water determination (Method I). For example, Karl Fischer Titrators V20/V30 (Mettler Toledo) may be used.

The titrimetric determination of water is based upon the quantitative reaction of water with an anhydrous solution of sulfur dioxide and iodine in the presence of a buffer that reacts with hydrogen ions according to the following reaction:

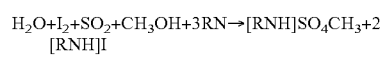

$$H_2O+I_2+SO_2+CH_3OH+3RN\rightarrow[RNH]SO_4CH_3+2[RNH]I$$

In Karl Fischer (KF) volumetric determination, a titrant containing iodine is gradually added to the water containing sample until the water is completely displaced and free iodine can be detected in the titration solution. The end point of the titration is recorded using bivoltametric indication.

It also forms part of the invention a single-dose pharmaceutical or veterinary liquid composition packaged in a blow-fill-seal (BFS) container, wherein the composition comprises a therapeutically effective amount of clotrimazole or a pharmaceutically or veterinary acceptable salt thereof, together with one or more pharmaceutically or veterinary acceptable excipients or carriers, with the condition that the water content of the composition is equal to or lower than 4% by weight with respect to the total composition weight.

All the embodiments mentioned above for the single-dose packaged composition also apply to the single-dose packaging unit and vice versa.

The invention also relates to a secondary packaging which comprises one or more single-dose packaging units as previously defined.

Typically, the secondary packaging may include from 1 to 30 single-dose packaging units (BFS containers). Thus, in one embodiment, optionally in combination with one or more features of the various embodiments described above or below, the secondary packaging of the invention comprises from 1 to 30 single-dose packaging units (BFS containers).

As mentioned above, when the oxygen content inside the secondary packaging is controlled, the stability of the liquid composition is even improved. Accordingly, in one embodiment, optionally in combination with one or more features of the various embodiments described above or below, the oxygen content inside the secondary packaging is equal to or lower than 10% by volume with respect to the total volume of gas content.

In another embodiment, optionally in combination with one or more features of the various embodiments described above or below, the oxygen content inside the secondary packaging is equal to or lower than 9%, equal to or lower than 8%, equal to or lower than 7%, equal to or lower than 6%, equal to or lower than 5%, equal to or lower than 4%, equal to or lower than 3%, equal to or lower than 2%, equal to or lower than 1%, equal to or lower than 0.5%, equal to or lower than 0.1%, or equal to 0.0%, by volume with respect to the total volume of gas content.

In another embodiment, optionally in combination with one or more features of the various embodiments described above or below, the oxygen content inside the secondary packaging is from 0.0 to 10%, from 0.0 to 9%, from 0.0 to 8%, from 0.0 to 7%, from 0.0 to 6%, from 0.0 to 5%, from 0.0 to 4%, from 0.0 to 3%, from 0.0 to 2%, from 0.0 to 1%, from 0.0 to 0.5%, or from 0.0 to 0.1% by volume with respect to the total volume of gas content.

The oxygen content inside the secondary packaging may be measured by using different methods including galvanic cell sensors (electrochemical cells) and polarographic sensors which are based on the electrochemical reaction of oxygen with an electrolyte to produce an electrical current, and optical sensors which use fiber optics and a fluorescence method to measure oxygen via spectrometry. For example, the oxygen content inside the secondary packaging may be measured by an electrochemical cell such as the headspace gas analyzer hand held for analysis of modified atmospheres in food and pharmaceutical packages OXYBABY®.

The expression "total volume of gas" as used herein refers to the total volume of gas inside the secondary packaging.

The secondary packaging may be made of a complex of aluminium foil and/or plastic films (polyethylene terephthalate (PET), polyethylene (PE), polypropylene (PP), polyethylene terephthalate glycol (PETG), Amorphous Polyethylene Terephthalate (APET), polyvinyl chloride (PVC)) and/ or paper and/or adhesive foil and/or resins. Non-limiting examples of secondary packaging include the materials PET/adhesive/aluminium/adhesive/PE, paper/adhesive/aluminium, aluminium/adhesive, paper/adhesive/aluminium/ PE, Paper/adhesive/PE/adhesive/aluminium, and the like.

Thus, in one embodiment, optionally in combination with one or more features of the various embodiments described above or below, the secondary packaging is an aluminium foil complex overwrap pouch.

One option to control the oxygen content inside of the single-dose packaging is to fill it with an inert gas. Non-limiting examples of inert gases which may be used for the purposes of the invention include nitrogen, argon, helium, and carbon dioxide. Thus, in another embodiment, optionally in combination with one or more features of the various embodiments described above or below, the secondary packaging which contains the BFS container comprises an inert gas, more particularly, the inert gas is selected from the group consisting of nitrogen, argon, helium, and carbon dioxide, and combinations thereof.

Alternatively, the oxygen content can be removed by applying vacuum or other pharmaceutical procedures in the secondary packaging. Thus, in one embodiment, optionally in combination with one or more features of the various embodiments described above or below, oxygen inside the secondary packaging is absent. In another embodiment, optionally in combination with one or more features of the various embodiments described above or below, gas inside the secondary packaging is absent.

The term "obtainable" is used herein for defining the container by its preparation process. For the purposes of the invention, the expressions "obtainable", "obtained" and similar equivalent expressions are used interchangeably and, in any case, the expression "obtainable" encompasses the expression "obtained".

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention.

The following examples are provided by way of illustration, and they are not intended to be limiting of the present invention. Furthermore, the present invention covers all possible combinations of particular and preferred embodiments described herein.

EXAMPLES

Example 1—Single-Dose Packaged Clotrimazole Solution in PEG (Water Content 1.2%)

Formula 1:

| INGREDIENTS | % (w/v) |
| --- | --- |
| Clotrimazole | 1% |
| Polyethylene Glycol 400 (PEG-400) | q.s. 100% |

Manufacture Process:

The single-dose packaged clotrimazole solution of this example was obtained in a BFS equipment Rommelag bp321M. Firstly, a solution of the active ingredient in PEG 400 at 40±15° C. was prepared. To sterilize the solution two sterilization filters (Polyvinylidene difluoride (PVDF) membrane filters, pore size 0.22 μm) were used. The integrity of these filters was checked before use, and the filters were dried at 70° C. for at least 5 hours. On the other hand, a holding tank was sterilized with vapour and after sterilization residual water was removed. The clotrimazole PEG solution was filtered through the first dried filter. After discarding the first liters of the filtered solution in order to minimize the presence of water in the solution which could come from the filter, the filtered solution was introduced in the first holding tank. Before starting the BFS process, the microbial count in room air was checked. The count was also monitored in the aseptic BFS cabinet area during the whole process. Pellets of LDPE (Lyondellbasell Purell PE 1840H) were loaded into the BFS hopper. The second sterilization filter was loaded into the BFS equipment. The BFS equipment was sterilized with water vapour. Then, sterilized air was passed through the BFS equipment in order to dry the product pipeline path after sterilization. The product was filtered and transferred to the buffer tank of the BFS equipment. Again, the first liters of filtered solution that could contain residual water were discarded (between 1-10 L). The water content of the product, measured by Karl Fischer USP 41 <921> (Method I, apparatus Volumetric Karl Fischer Titrator Mettler Toledo V20S), was 1.2% by weight with respect to the total composition weight. The BFS filling process was carried out by dosing 0.2 mL of the solution into the thermoformed vials of LDPE which have a total volume capacity of 0.7 mL. The packaging process was completed with a secondary packaging (overwrap aluminium foil complex pouches, Constantia Flexibles). The oxygen content inside the secondary package was not controlled.

Example 2—Single-Dose Packaged Clotrimazole Solution in PEG (Water Content 0.8%, Oxygen Content <10%)

Formula 1:

| INGREDIENTS | % (w/v) |
|---|---|
| Clotrimazole | 1% |
| Polyethylene Glycol 400 (PEG-400) | q.s. 100% |

Manufacture Process:

The single-dose packaged clotrimazole solution of example 2 was prepared as described in example 1, except by the fact that a stream of nitrogen was used during the sealing of the secondary packaging (overwrap aluminium foil complex pouches). The water content of the product, measured by Karl Fischer USP 41 <921> (Method I, apparatus Volumetric Karl Fischer Titrator Mettler Toledo V20S), was 0.8% by weight with respect to the total composition weight, and the oxygen content inside the secondary package, measured by the headspace gas analyzer OXYBABY®, was lower than 10% by volume with respect to the total volume of gas content inside the secondary package.

Comparative Example 1—Single-Dose Packaged Clotrimazole Solution in PEG (Water Content 5.2% (F1 Batch SVT12), and 5.6% (F1 Batch SVT13)

Formula 1:

| INGREDIENTS | % (w/v) |
|---|---|
| Clotrimazole | 1% |
| Polyethylene Glycol 400 (PEG-400) | q.s. 100% |

Manufacture Process:

Two batches were prepared as described in example 1, except by the fact that after filtration of the solution through filters, no filtered solution was discarded. The water content of the product, (measured by Karl Fischer USP 41 <921> (Method I, apparatus Volumetric Karl Fischer Titrator Mettler Toledo V20S), was 5.2% (F1 Batch SVT12), and 5.6% (F1 Batch SVT13) by weight with respect to the total composition weight.

Comparative Example 2—Multi-Dose Packaged Clotrimazole Solution in PEG

Formula 1:

| INGREDIENTS | % (w/v) |
|---|---|
| Clotrimazole | 1% |
| Polyethylene Glycol 400 | q.s. 100% |

Manufacture Process:

The active ingredient was dissolved in PEG 400 under stirring at 40° C.±15° C. until obtaining a transparent solution. Bottles of LDPE having a total volume capacity of 10 mL were filled with the clotrimazole solution following a conventional pharmaceutical process.

Stability Assays

The stability of the clotrimazole compositions described above was tested at the storage conditions of 40° C./<25% RH for a period of 2 months (samples were analyzed at 0, 1 and 2 months). Chemical stability was measured by the HPLC method described in the USP 41 (monograph 'Clotrimazole Topical Solution') in apparatus Agilent 1100 series. The clotrimazole composition of comparative example 1 was additionally analysed after storage for 30 months at room temperature. The obtained results are shown in the tables below:

TABLE 1

Example 1 single-dose packaged composition (water content 1.2%)

| Component | Acceptance criteria | Stability (40° C., <25% RH) | | |
|---|---|---|---|---|
| | | Initial | 1 month | 2 months |
| Clotrimazole | 90.0-115.0% | 99.2 | 96.9 | 95.7 |
| Imidazole | ≤0.50% | <0.05 | 0.14 | 0.48 |
| (2-chlorophenyl)diphenylmethanol | ≤0.50% | <0.05 | 0.19 | 0.39 |
| Total degradation products | ≤2.0% | <0.05 | 0.40 | 1.2 |

TABLE 2

Example 2 single-dose packaged composition (water content 0.8% and oxygen content <10%)

| Component | Acceptance criteria | Stability (40° C., <25% RH) | | |
|---|---|---|---|---|
| | | Initial | 1 month | 2 months |
| Clotrimazole | 90.0-115.0% | 98.8 | 99.2 | 100.2 |
| Imidazole | ≤0.50% | <0.05 | 0.09 | 0.13 |
| (2-chlorophenyl)diphenylmethanol | ≤0.50% | <0.05 | 0.09 | 0.08 |
| Total degradation products | ≤2.0% | <0.05 | 0.24 | 0.21 |

TABLE 3

Comparative example 1 single-dose packaged composition (water content 5.2% (F1 Batch SVT12), and 5.6% (F1 Batch SVT13))

| | | Stability room temperature 30 months | |
|---|---|---|---|
| Component | Acceptance criteria | F1 Batch SVT12 | F1 Batch SVT13 |
| Clotrimazole | 90.0-115.0% | <80% | <80% |
| Imidazole | ≤0.50% | >10% | >10% |
| (2-chlorophenyl)diphenylmethanol | ≤0.50% | >10% | >10% |
| Total degradation products | ≤2.0% | >20% | >20% |

TABLE 4

Comparative example 1 single-dose packaged composition (water content 5.2% (F1 Batch SVT12), and 5.6% (F1 Batch SVT13))

| | | Stability (40° C., <25% RH) 2 months | |
|---|---|---|---|
| Component | Acceptance criteria | F1 Batch SVT12 | F1 Batch SVT13 |
| Clotrimazole | 90.0-115.0% | 92.8% | 92.8% |
| Imidazole | ≤0.50% | 1.4% | 1.4% |
| (2-chlorophenyl)diphenylmethanol | ≤0.50% | 2.0% | 1.9% |
| Total degradation products | ≤2.0% | 5.1% | 5.0% |

TABLE 5

Comparative example 2 multi-dose packaged composition

| | | Stability (40° C., <25% RH) | | |
|---|---|---|---|---|
| Component | Acceptance criteria | Initial | 1 month | 2 months |
| Clotrimazole | 90.0-115.0% | 99.4 | 97.8 | 97.0 |
| Imidazole | ≤0.50% | <0.05 | <0.05 | <0.05 |
| (2-chlorophenyl)diphenylmethanol | ≤0.50% | <0.05 | <0.05 | <0.05 |
| Total degradation products | ≤2.0% | <0.05 | <0.05 | <0.05 |

As can be seen, when the water content in the single-packaged compositions was not controlled, significant degradation was observed beyond acceptable levels (see tables 3 and 4). By contrast, when the water content was controlled (see tables 1 and 2), stability complied with the acceptance criteria as in the case of the composition placed in the multi-dose container (see table 5). Furthermore, the stability behaviour even improved more when the oxygen content inside the secondary packaging was controlled below 10% (table 2).

CITATION LIST

US20090011045
US20150297588
United States Pharmacopeia USP 41 <71> Sterility Test (pages 5984-5991)
United States Pharmacopeia USP 41 (monograph 'Clotrimazole Topical Solution') (pages 1044-1045)
United States Pharmacopeia USP 41 <921> Water determination (pages 6687-6692)

For reasons of completeness, various aspects of the invention are set out in the following numbered clauses:

Clause 1. A single-dose pharmaceutical or veterinary liquid composition packaged in a blow-fill-seal (BFS) container, wherein the composition comprises a therapeutically effective amount of clotrimazole or a pharmaceutically or veterinary acceptable salt thereof, together with one or more pharmaceutically or veterinary acceptable excipients or carriers, with the condition that the water content of the composition is equal to or lower than 4% by weight with respect to the total composition weight.

Clause 2. Single-dose composition according to clause 1, wherein the therapeutically effective amount of clotrimazole is from 0.1 to 5% by weight with respect to the total composition volume.

Clause 3. Single-dose composition according to any of clauses 1-2, wherein the composition comprises a solubilizing agent which is selected from the group consisting of oils, ($C_1$-$C_{18}$) alkyl esters of ($C_4$-$C_{28}$) fatty acids, glycerides, polyhydric alcohols, and mixtures thereof.

Clause 4. Single-dose composition according to clause 3, wherein the solubilizing agent is selected from the group consisting of liquid paraffin, light liquid paraffin, argan oil, corn oil, palm oil, coconut oil, cottonseed oil, peanut oil, rapeseed oil, sunflower oil, sesame oil, soybean oil, safflower oil, almond oil, castor oil, olive oil, ethyl oleate, decyl oleate, isopropyl myristate, isopropyl palmitate, isopropyl isostearate, isostearyl isostearate, myristyl lactate, caprylic triglyceride, caprylic/capric triglyceride, caproic triglyceride, capric acid triglyceride, lauric triglyceride, lauric/caprylic/capric triglyceride, ethylene glycol, diethylene glycol, triethylene glycol, polyethylene glycols, propylene glycol, dipropylene glycol, polypropylene glycols, butylene glycols, glycerol, diglycerol, polyglycerols, and mixtures thereof.

Clause 5. Single-dose composition according to clause 4, wherein the solubilizing agent is polyethylene glycol.

Clause 6. Single-dose composition according to clause 5, wherein the polyethylene glycol is selected from the group consisting of PEG 200, PEG 300, PEG 400, PEG 600, and mixtures thereof.

Clause 7. Single-dose composition according to any of clauses 1-6, wherein the blow-fill-seal (BFS) container is made of a thermoplastic polymer selected from the group consisting of polyethylene (PE), low density polyethylene (LDPE), high density polyethylene (HDPE), polypropylene (PP) and mixtures thereof.

Clause 8. Single-dose composition according to any of clauses 1-7, which is sterile.

Clause 9. Single-dose composition according to any of clauses 1-8, wherein the water content of the composition is equal to or lower than 3% by weight with respect to the total composition weight.

Clause 10. Secondary packaging comprising one or more single-dose compositions packaged in blow-fill-seal (BFS) containers as defined in any of clauses 1-9.

Clause 11. Secondary packaging according to clause 10, wherein the oxygen content inside the secondary packaging is equal to or lower than 10% by volume with respect to the total volume of gas.

Clause 12. Secondary packaging according to clause 10, wherein the oxygen content inside the secondary packaging is equal to or lower than 5% or equal to or lower than 2%, by volume with respect to the total volume of gas.

Clause 13. Secondary packaging according to any of clauses 10-12, which is an aluminium foil complex overwrap pouch.

Clause 14. Secondary packaging according to any of clauses 10-13, which comprises an inert gas.

Clause 15. Secondary packaging according to any of clauses 10-13, wherein gas inside the secondary packaging is absent.

The invention claimed is:

1. A single-dose packaging unit which is a blow-fill-seal (BFS) container which comprises a sterile pharmaceutical or veterinary liquid composition which is a solution, wherein:
   a) the composition comprises a therapeutically effective amount of clotrimazole or a pharmaceutically or veterinary acceptable salt thereof, together with one or more pharmaceutically or veterinary acceptable excipients or carriers, wherein clotrimazole is the single active ingredient of the composition, and a solubilizing agent which is polyethylene glycol, and
   b) the container has a volume from 0.05 to 8 mL, with the condition that a water content of the composition is equal to or lower than 4% by weight with respect to the total composition weight.

2. The single-dose packaging unit according to claim 1, wherein the therapeutically effective amount of clotrimazole is from 0.1 to 5% by weight with respect to the total composition volume.

3. The single-dose packaging unit according to claim 1, wherein the polyethylene glycol is selected from the group consisting of PEG 200, PEG 300, PEG 400, PEG 600, and mixtures thereof.

4. The single-dose packaging unit according to claim 1, wherein the blow-fill-seal (BFS) container is made of a thermoplastic polymer selected from the group consisting of polyethylene (PE), low density polyethylene (LDPE), high density polyethylene (HDPE), polypropylene (PP) and mixtures thereof.

5. The single-dose packaging unit according to claim 1, which is sterile.

6. The single-dose packaging unit according to claim 1, wherein the water content of the composition is equal to or lower than 3% by weight with respect to the total composition weight.

7. A secondary packaging comprising one or more single-dose packaging units as defined in claim 1.

8. The secondary packaging according to claim 7, wherein an oxygen content inside the secondary packaging is equal to or lower than 10% by volume with respect to the total volume of gas.

9. The secondary packaging according to claim 7, wherein an oxygen content inside the secondary packaging is equal to or lower than 5% or equal to or lower than 2%, by volume with respect to the total volume of gas.

10. The secondary packaging according to claim 7, which is an aluminium foil complex overwrap pouch.

11. The secondary packaging according to claim 7, which comprises an inert gas.

12. The secondary packaging according to claim 7, wherein gas inside the secondary packaging is absent.

13. The single-dose packaging unit according to claim 4, wherein the thermoplastic polymer is low density polyethylene (LDPE).

14. The single-dose packaging unit according to claim 1, wherein the therapeutically effective amount of clotrimazole is from 0.1 to 5% by weight with respect to the total composition volume, and the blow-fill-seal (BFS) container is made of a thermoplastic polymer selected from the group consisting of polyethylene (PE), low density polyethylene (LDPE), high density polyethylene (HDPE), polypropylene (PP) and mixtures thereof.

15. The single-dose packaging unit according to claim 14, wherein the polyethylene glycol is selected from the group consisting of PEG 200, PEG 300, PEG 400, PEG 600, and mixtures thereof.

16. The single-dose packaging unit according to claim 15, wherein the water content of the composition is equal to or lower than 3% by weight with respect to the total composition weight.

17. The single-dose packaging unit according to claim 16, wherein the thermoplastic polymer is low density polyethylene (LDPE).

* * * * *